(12) United States Patent
Chen et al.

(10) Patent No.: US 7,534,606 B2
(45) Date of Patent: May 19, 2009

(54) PLACENTAL STEM CELL AND METHODS THEREOF

(75) Inventors: Yao-Chang Chen, Taipei (TW); Lin-Ju Yen, Taipei (TW); Chih-Cheng Chien, Taipei (TW); Hsing-I Huang, Taichung (TW)

(73) Assignee: National Health Research Institutes (TW)

( * ) Notice: Subject to any disclaimer, the term of this patent is extended or adjusted under 35 U.S.C. 154(b) by 275 days.

(21) Appl. No.: 11/201,295

(22) Filed: Aug. 11, 2005

(65) Prior Publication Data

US 2006/0030039 A1    Feb. 9, 2006

Related U.S. Application Data

(63) Continuation-in-part of application No. 11/032,153, filed on Jan. 11, 2005.

(60) Provisional application No. 60/535,502, filed on Jan. 12, 2004.

(51) Int. Cl.
*C12N 5/00* (2006.01)

(52) U.S. Cl. .................. 435/377; 435/325; 435/375

(58) Field of Classification Search .................. None
See application file for complete search history.

(56) References Cited

U.S. PATENT DOCUMENTS

| | | |
|---|---|---|
| 5,486,359 A | 1/1996 | Caplan et al. |
| 5,965,436 A | 10/1999 | Thiede et al. |
| 6,022,540 A | 2/2000 | Bruder et al. |
| 6,165,785 A | 12/2000 | Ogle et al. |
| 6,197,585 B1 | 3/2001 | Stringer et al. |
| 6,562,619 B1 | 5/2003 | Gearhart et al. |
| 2002/0123141 A1 | 9/2002 | Hariri |
| 2003/0032179 A1 | 2/2003 | Hariri |
| 2003/0180269 A1 | 9/2003 | Hariri |
| 2004/0151701 A1 | 8/2004 | Kim et al. |
| 2005/0176139 A1 | 8/2005 | Chen |

FOREIGN PATENT DOCUMENTS

WO    WO 03/042405 A2    5/2003

OTHER PUBLICATIONS

Long X et al. 2005. Neural cell differentiation in vitro from adult human bone marrow mesenchymal stem cells. Stem Cells Dev. 14: 65-69.*

Zhang Y et al. 2004. Comparison of mesenchymal stem cells from human placenta and bone marrow. Chin Med J (Engl) 117: 882-887.*

Yin F et al. 2004. Differentiation of mesenchymal stem cells into early neuron-like cells. Zhongguo Linchuang Kangfu 8: 786-787.*

Barry, F. et al., "Chondrogenic differentiation of mesenchymal stem cells from bone marrow: differentiation-dependent gene expression of matrix components," Exp. Cell Res. 268:189-200 (2001).

Migliaccio, A.R. et al., "Cell dose and speed of engraftment in placental/umbilical cord blood transplantation: graft progenitor cell content is a better predictor than nucleated cell quantity," Blood 96:2717-2722 (2000).

Rubinstein, P. et al., "Outcomes among 562 recipients of placental-blood transplants from unrelated donors," N. Engl. J. Med. 339:1565-1577 (1998).

Zuk, P.A. et al., "Multilineage cells from human adipose tissue: implications for cell-based therapies," Tissue Engineering 7:211-228 (2001).

Azizi, S.A. et al., "Engraftment and Migration of Human Bone Marrow Stromal Cells Implanted in the Brains of Albino Rats—Similarities to Astrocyte Grafts," *Proc. Natl. Acad. Sci. U.S.A.*, 95:3908-3913 (1998).

Bailo, M. et al., "Engraftment Potential of Human Amnion and Chorion Cells Derived From Term Placenta," *Transplantation* 78:1439-1448 (2004).

Buzanska, L. et al., "Human Cord Blood-Derived Cells Attain Neuronal and Glial Features In Vitro," *J. Cell Sci.*, 115:2131-2138 (2002).

Cox, M.E. et al., "Acquisition of Neuroendocrine Characteristics by Prostate Tumor Cells is Reversible: Implications for Prostate Cancer Progression," *Cancer Res.*, 59:3821-3830 (1999).

Deng, W. et al., "In Vitro Differentiation of Human Marrow Stromal Cells Into Early Progenitors of Neural Cells by Conditions That Increase Intracellular Cyclic AMP," *Biochem. Biophys. Res. Commun.*, 282:148-152 (2001).

Fukuchi, Y. et al., "Human Placenta-Derived Cells Have Mesenchymal Stem/Progenitor Cell Potential," *Stem Cells* 22:649-658 (2004).

Goodwin, H.S. et al., "Multilineage Differentiation Activity by Cells Isolated From Umbilical Cord Blood: Expression of Bone, Fat, and Neural Markers," *Biol. Blood Marrow Transplant*. 7:581-588 (2001).

(Continued)

Primary Examiner—Lora E Barnhart
(74) Attorney, Agent, or Firm—Finnegan, Henderson, Farabow, Garrett & Dunner, LLP

(57) ABSTRACT

The present invention describes stem cells obtained from post-partum placenta and their methods of obtaining and culturing. The present invention also describes compositions comprising placental stem cells and methods of using placental stem cells.

5 Claims, 12 Drawing Sheets

OTHER PUBLICATIONS

Ha, Y. et al., "Neural Phenotype Expression of Cultured Human Cord Blood Cells in Vitro," *Neuroreport* 12:3523-3527 (2001).

Hunter, K. et al., "Retinoic Acid Stimulates Neurite Outgrowth in the Amphibian Spinal Cord," *Proc. Natl. Acad. Sci. U.S.A.* 88:3666-3670 (1991).

In 'T Anker, P.S. et al., "Isolation of Mesenchymal Stem Cells of Fetal or Maternal Origin From Human Placenta," *Stem Cells* 22:1338-1345 (2004).

Kogler, G. et al., "A New Human Somatic Stem Cell From Placental Cord Blood With Intinsic Pluripotent Differentiation Potential," *J. Exp. Med.* 200:123-135 (2004).

Kopen, G.C. et al., "Marrow Stromal Cells Migrate Throughout Forebrain and Cerebellum, and They Differentiate Into Astrocytes After Injection Into Neonatal Mouse Brains," *Proc. Natl. Acad. Sci. U.S.A.* 96:10711-10716 (1999).

Lee, O.K. et al., "Isolation of Multipotent Stem Cells From Umbilical Cord Blood," *Blood* 103:1669-1675 (2004).

Maric, D. et al., "Prospective Cell Sorting of Embryonic Rat Neural Stem Cells and Neuronal and Glial Progenitors Reveals Selective Effects of Basic Fibroblast Growth Factor and Epidermal Growth Factor on Self-Renewal and Differentiation," *J. Neurosci.* 23:240-251 (2003).

Miyamoto, K. et al., "Human Placenta Feeder Layers Support Undifferentiated Growth of Primate Embryonic Stem Cells," *Stem Cells* 22:433-440 (2004).

Pittenger, M.F. et al., "Multilineage Potential of Adult Human Mesenchymal Stem Cells," *Science* 284:143-147 (1999).

Ryden, M. et al., "Functional Characterization of Human Mesenchymal Stem Cell-Derived Adipocytes," *Biochem. Biophys. Res. Commun.* 311:391-397 (2003).

Sanchez-Ramos, J. et al., "Adult Bone Marrow Stromal Cells Differentiate Into Neural Cells In Vitro," *Exp. Neurol.*, 164:247-256 (2000).

Woodbury, D. et al., "Adult Rat and Human Bone Marrow Stromal Cells Differentiate Into Neurons," *J. Neurosci. Res.*, 61:364-370 (2000).

Woodbury, D. et al., "Adult Bone Marrow Stromal Stem Cells Express Germline, Ectodermal, Endodermal, and Mesodermal Genes Prior to Neurogenesis," *J. Neurosci. Res.*, 96:908-917 (2002).

Yen, B.L. et al., "Isolation of Multipotent Cells from Human Term Placenta," *Stem Cells* 23:3-9 (2005).

Deng et al., "In Vitro Differentiation of Human Marrow Stromal Cells into Early Progenitors of Neural Cells by Conditions That Increase Intracellular Cyclic AMP," *Biochemical and Biophysical Research Communications*, 282: 148-152 (2001).

* cited by examiner

CD14  CD45  CD34

CD90  CD105  STRO-1

Tuj1

GFAP

NeuN

Untreat

RA

IBMX

PLACENTAL STEM CELL AND METHODS THEREOF

RELATED APPLICATION

This application is a continuation-in-part application of U.S. application Ser. No. 11/032,153, filed Jan. 11, 2005, which claims the benefit of U.S. Provisional Application No. 60/535,502, filed Jan. 12, 2004, the contents of both of which are incorporated herein by reference.

DESCRIPTION OF THE INVENTION

1. Field of the Invention

The present invention relates to stem cells obtained from the post-partum placenta and their methods of obtaining and culturing. The present invention further relates to compositions comprising placental stem cells and to methods of using placental stem cells.

2. Background of the Invention

Stem cells have the potential to develop into many different cell types in the body. Stem cells can theoretically divide without limit to replenish other cells. When a stem cell divides, each new cell has the potential to either remain a stem cell or become another type of cell with a more specialized function, such as a muscle cell, a red blood cell, or a brain cell. Stem cells are often classified as totipotent, pluripotent, and multipotent. A totipotent stem cell has differentiation potential which is total: it gives rise to all the different types of cells in the body, including the germ cells. A fertilized egg cell is an example of a totipotent stem cell. Pluripotent stem cells can give rise to any type of cell in the body except those needed to develop a fetus. Multipotent stem cells can give rise to two or more different cell types but only within a given organ or tissue type. In contrast to stem cells, progenitor cells are unable to self-renew and they give rise to only a few cell types.

The main sources of stem cells are the embryonic stem cells and adult stem cells. Embryonic stem cells are derived from embryos. For research purposes, embryonic stem cells are obtained from embryos that have developed from eggs that have been fertilized in vitro (such as at an in vitro fertilization clinic) and then donated for research purposes with informed consent of the donors. The embryos are typically obtained at four or five days old when they are a hollow microscopic ball of cells called the blastocyst. The blastocyst includes three structures: the trophoblast, which is the layer of cells that surrounds the blastocyst; the blastocoel, which is the hollow cavity inside the blastocyst; and the inner cell mass, which is a group of approximately 30 cells at one end of the blastocoel.

The embryonic stem cells are obtained by isolating the inner cell mass and growing them in vitro. The inner cell mass is usually grown on a layer of feeder cells, which are mouse embryonic fibroblasts that serve as an adherent layer for the inner cell mass and as a source of nutrients. Embryonic stem cells are pluripotent and can become all cell types of the body.

An adult stem cell, or a somatic stem cell, is an undifferentiated cell found among differentiated cells in a tissue or organ. An adult stem cell can renew itself and can differentiate into specialized cell types of the tissue or organ. They are believed to reside in a specific area of each tissue where they may remain quiescent (non-dividing) for many years until they are activated by disease or tissue injury. Adult stem cells are present in very small numbers in each tissue and have been found in various tissues and organ, including the brain, bone marrow, peripheral blood, blood vessels, skeletal muscle, skin, umbilical cord, adipose tissue, amnion, and liver.

Stem cells have gained considerable interest as a treatment for a myriad of diseases, conditions, and disabilities because they provide a renewable source of cells and tissues. Blood-forming stem cells in bone marrow called hematopoietic stem cells (HSCs) are currently the only type of stem cell commonly used. HSCs are used to treat leukemia, lymphoma and several inherited blood disorders. However, other stem cells have considerable potential for treating many other diseases. A number of reports have suggested that certain adult stem cell types have the ability to differentiate into multiple cell types. For example, hematopoietic stem cells may differentiate into brain cells (neurons, oligodendrocytes, and astrocytes) (Hao et al., H. Hemathother. Stem Cell Res. 12:23-32, 2003; Zhao et al., PNAS 100:2426-2431, 2003; Bonilla et al., Eur. J. Neurosci. 15:575-582, 2002), skeletal muscle cells (Ferrari et al., Science 279:1528-1530, 1998; Gussoni et al., Nature 401:390-394, 1999), cardiac muscle cells (Jackson et al., J. Clin. Invest. 107:1395-1402, 2001), and liver cells (Lagasse et al., Nat. Med. 6:1229-1234, 2000). Bone marrow stromal cells may differentiate into cardiac muscle cells and skeletal muscle cells (Galmiche et al., Blood 82:66-76, 1993; Wakitani et al., Muscle Nerve 18:1417-1426, 1995), while brain stem cells may differentiate into blood cells (Bjornson et al., Science 283:534-547, 1999) and skeletal muscle cells (Galli et al., Nat. Neurosci. 3:986-991, 2000).

Embryonic and adult stem cells each have advantages and disadvantages regarding potential use for cell-based regenerative therapies. An advantage of adult stem cells is that the patient's own cells may be expanded in culture and reintroduced into the patient. The use of the patient's own adult stem cells would prevent rejection of the cells by the immune system without having to use immunosuppressive drugs. In contrast, embryonic stem cells from a donor introduced into a patient could cause transplant rejection.

Conversely, embryonic stem cells can become all cell types of the body while adult stem cells are generally limited to differentiating into cell types of their tissue of origin, although, as discussed above, some evidence suggests that adult stem cell may differentiate into other cell types. Additionally, relatively large numbers of embryonic stem cells may be grown in culture, while adult stem cells are more rare in adult tissues and it is difficult to expand their numbers in cell culture. In this respect, embryonic stem cells are more advantageous because large numbers of cells are usually needed for stem cell replacement therapies.

However, the use of embryonic stem cells is controversial because of its implications on life. Embryonic stem cells are often obtained from supernumerary embryos from in vitro fertilization programs or from donated gametes. In contrast, adult stem cells pose no ethical dilemma, but their proliferative and differentiation capacity are less than those of embryonic stem cells. Moreover, invasive procedures are usually required to obtain adult stem cells. In addition, embryonic stem cells can cause teratoma formation, a benign tumor consisting of all three germ layers, whereas adult stem cells do not.

Neural stem cells (NSCs) are examples of adult stem cells. These stem cells have the ability to differentiate into all three cell types of the nervous system: neurons, astrocytes, and oligodendrocytes. NSCs can be isolated from either adult or fetal central nervous system tissues (Deacon et al., Exp. Neurol., 149:2841, 1998; Reynolds & Weiss, Dev. Biol., 175:1-13, 1996; Gage, Science, 287:1433-1438, 2000). Implanted NSCs can successfully survive and differentiate into neurons and glia, increasing the possibility of their therapeutic potential (Renfranz et al., Cell 66:713-729, 1991; Gage et al., Proc. Natl. Acad. Sci. U.S.A., 92:11879-11883, 1995; Lundberg et al., Brain Res., 737:295-300, 1996; Svendsen et al., Dev. Brain. Res., 99:253-258, 1997). However, the need for invasive intracranial sampling from adult brain, ethical concerns with fetal-derived cells, and immunological compatibility issues limit the clinical application of NSCs.

SUMMARY OF THE INVENTION

The present invention provides stem cells from the post-partum placenta. One aspect of the invention provides a method for obtaining a placental stem cell comprising: obtaining a post-partum placenta; preparing a single-cell suspension of placental cells; culturing the placental cells; and obtaining a placental stem cell. The placental stem cell may be multipotent or pluripotent and the placenta may be human placenta.

Another aspect of the invention provides a method for culturing a placental stem cell comprising: obtaining a post-partum placenta; preparing a single-cell suspension of placental cells; culturing the placental cells; obtaining a placental stem cell; and culturing the placental stem cell. The placental stem cell may be multipotent or pluripotent and the placenta may be human placenta.

A further aspect of the present invention provides an isolated placental stem cell having certain characteristics, including cell markers. Another aspect of the invention provides an isolated, homogeneous population of multipotent or pluripotent placental stem cells having certain characteristics, including cell markers.

Thus, an aspect of the invention also provides a method for obtaining a placental stem cell based on certain cell marker characteristics.

Yet, another aspect of the invention provides cryopreserved placental stem cells obtained from a post-partum placenta.

The present invention also provides a method for differentiation of placental stem cells. The placental stem cells may be obtained by the method of the invention. One aspect of the invention provides a method of adipocytic differentiation and another aspect provides a method of osteogenic differentiation of the placental stem cells. Yet another aspect provides a method of chondrogenic differentiation, and a further aspect of the invention provides a method of neurogenic differentiation.

Other aspects of the invention provide a composition comprising a placental stem cell and/or a differentiated placental stem cell and a pharmaceutical composition comprising a placental stem cell and/or a differentiated placental stem cell. The invention also provides a method of treating a patient comprising administering to the patient an effective amount of a placental stem cell and/or a differentiated stem cell.

BRIEF DESCRIPTION OF THE DRAWINGS

FIG. 2 FIG. 2 shows the staining of placental stem cells of the invention to demonstrate their differentiation potential into other cell types.

FIG. 3 FIG. 3 demonstrates the chondrogenic potential of the placental stem cells of the invention.

FIG. 5A shows the expression of Nestin by RT-PCR and FIG. 5B shows the expression of Oct-4 by RT-PCR. GAPDH served as an internal control for the RT-PCR reactions. FIGS. 5C and 5D show the expression of Nestin and Oct-4, respectively, by immunofluorescence.

FIGS. 7A and 7B show cells cultured in expansion medium, which were used as negative controls. FIGS. 7C and 7D show cells cultured in the presence of retinoic acid (RA). FIGS. 7E and 7F show cells cultured in the presence of IBMX. FIGS. 7A, 7C, and 7E are in phase contrast and FIGS. 7B, 7D, and 7F show immunocytochemical staining for NSE.

FIGS. 8A, 8B, and 8C show phase contrast photographs of placental stem cells cultured in the presence of IBMX for 24 hours, 72 hours, and 108 hours, respectively. Photographs were taken at a magnification of 200×. FIG. 8D shows the expression of NF-L by RT-PCR (top panel) at 0, 6 hours, three days, and five days after treatment with IBMX. GAPDH served as an internal control for the RT-PCR reactions (bottom panel).

FIG. 9A shows staining with MAP2, FIG. 9B shows staining with GFAP, and FIG. 9C shows staining with NG2.

FIGS. 10A-10C and 10D-10F each show the same field of cells. FIG. 10A shows immunostaining with anti-MAP2 antibody. FIG. 10B shows the same cells stained with CM-Dil. FIG. 10C shows the nuclei of the same cells stained with DAPI. FIG. 10D shows immunostaining with anti-GFAP antibody. FIG. 10E shows the same cells stained with CM-Dil. FIG. 10F shows the nuclei of the same cells stained with DAPI.

DESCRIPTION OF THE EMBODIMENTS

Figure 1A:
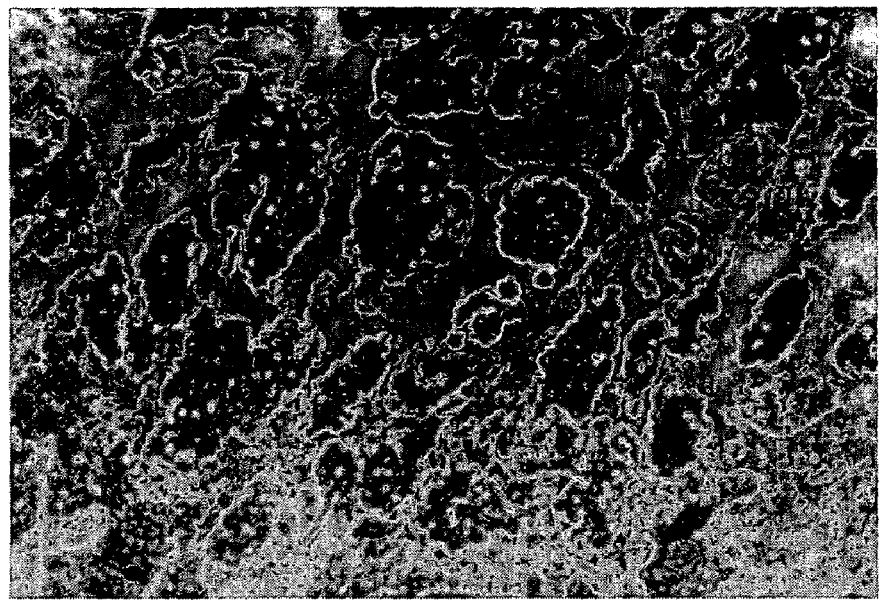
FIG. 1 FIG. 1 shows the staining of control bone marrow mesenchymal stem cells as a positive control for Oil Red staining, which detects adipocytic differentiation in red (FIG. 1A, shaded areas), and von Kossa staining, which detects osteogenic differentiation in brown (FIG. 1B, darker shaded areas).

The present invention provides stem cells from post-partum placenta. The placenta provides a rich source of stem cells and growth factors because it is of fetal origin and derived from the embryo. Therefore, placental stem cells may be more likely to have a higher proliferative and differentiation capacity than other adult stem cells. Moreover, the placenta is a temporary organ used to ensure fetal survival in utero and is discarded after birth. Placenta obtained postpartum therefore poses no ethical controversy and no invasive procedure is required for procurement of the cells.

The embodiments described and the terminology used herein are for the purpose of describing exemplary embodiments only, and are not intended to be limiting. The scope of the present invention is intended to encompass additional embodiments not specifically described herein, but that would be apparent to one skilled in the art upon reading the present disclosure and practicing the invention.

The present invention relates to stem cells from the post-partum placenta. As used herein, the term "stem cell" refers to a master cell that can reproduce indefinitely to form the specialized cells of tissues and organs. A stem cell can divide to produce two daughter stem cells, or one daughter stem cell and one progenitor ("transit") cell, which then proliferates into the tissue's mature, fully formed cells. As used herein, the term "stem cell" includes multipotent and pluripotent stem cells.

As used herein, the term "pluripotent cell" refers to a cell that has complete differentiation versatility, i.e., the capacity to grow into any of the mammalian body's cell types, except those needed to develop a fetus. A pluripotent cell can be self-renewing, and can remain dormant or quiescent within a tissue.

As used herein, the term "multipotent cell" refers to a cell that has the capacity to grow into two or more different cell types of the mammalian body within a given tissue or organ. However, a multipotent cell may have the capacity to be pluripotent. For example, hematopoietic stem cells were originally believed to be multipotent cells, i.e., stem cells that could develop into several types of blood cells, but not into brain cells. However, as discussed above, recent evidence suggests that hematopoietic stem cells may be pluripotent because they may differentiate into other types of cells, including brain cells.

As used herein, the term "progenitor cell" refers to a cell that is committed to differentiate into a specific type of cell or to form a specific type of tissue.

As used herein, the term "post-partum placenta" refers to placenta that has been expunged from the uterus after birth and does not include the umbilical cord. Thus, the method of the present invention for obtaining placental stem cells contrasts from prior methods utilizing umbilical cord blood (Migliaccio et al., Blood 96:2717-2722, 2000; Rubinstein et al., New England J Medicine 339:1565-1577, 1998; Hariri et al., U.S. Patent Publication No.: 20030180269) or the umbilical cord itself. The placenta may be obtained from any mammalian species, including rodents, human, non-human primates, equines, canines, felines, bovines, porcines, ovines, lagomorphs, and the like. In an embodiment of the invention, the placenta is obtained from human.

A placental stem cell may be characterized by its cell markers. A variety of cell markers are known. See e.g., *Stem Cells: Scientific Progress and Future Research Directions*. Department of Health and Human Services. June 2001. http://www.nih.gov/news/stemcell/scireport.htm. Cell markers may be detected by methods known in the art, such as by immunochemistry or flow cytometry. Flow cytometry allows the rapid measurement of light scatter and fluorescence emission produced by suitably illuminated cells or particles. The cells or particles produce signals when they pass individually through a beam of light. Each particle or cell is measured separately and the output represents cumulative individual cytometric characteristics. Antibodies specific to a cell marker may be labeled with a fluorochrome so that it may be detected by the flow cytometer. See, eg., Bonner et al., Rev. Sci. Instrum 43:404-409, 1972; Herzenberg et al., Immunol. Today 21:383-390, 2000; Julius et al, PNAS 69:1934-1938, 1972; Ormerod (ed.), *Flow Cytometry: A Practical Approach*, Oxford Univ. Press, 1997; Jaroszeski et al. (eds.), *Flow Cytometry Protocols* in Methods in Molecular Biology No. 91, Humana Press, 1997; *Practical Flow Cytometry*, $3^{rd}$ ed., Wiley-Liss, 1995.

In an embodiment of the invention, human placental stem cell expresses at least one of the following cell markers: CD9, CD13, CD29, CD44, CD90/Thy-1, CD105/SH-2/endoglin, CD166, SH-3, SH-4, vimentin, HLA-ABC, SSEA-4, TRA-1-60, and TRA-1-81. In a further embodiment, a human placental stem cell is negative for the at least one of the following cell markers: CD14, CD34, CD45, AC or CD133/2, cytokeratin 7, von Willebrand factor, HLA-DR, HLA G, glycophorin A, placental alkaline phosphatase, and β-human chorionic gonadotropin. In another embodiment of the invention, a placental stem cell is positive for at least CD9, CD13, CD29, CD44, CD90/Thy-1, CD105/SH-2/endoglin, CD166, SH-3, SH-4, vimentin, HLA-ABC, SSEA4, TRA-1-60, and TRA-1-81, and negative for at least CD14, CD34, CD45, AC or CD133/2, cytokeratin 7, von Willebrand factor, HLA-DR, HLA G, glycophorin A, placental alkaline phosphatase, and β-human chorionic gonadotropin.

The present invention also embodies a homogeneous population of placental stem cells. As used herein, "population of cells" refers to a unit comprising at least two cells. "Homogeneous population" refers to a population of cells exhibiting substantially the same phenotype, such as that determined by cell markers. A homogeneous population may comprise at least about 70% of substantially the same cells, or at least about 80%, 90%, 92%, 96%, or 99% of substantially the same cells.

The present invention therefore provides a method of obtaining a placental stem cell by isolating placental cells having certain cell characteristics. The placental cells having these cell characteristics may be isolated from the single-cell suspension of placental cells obtained from post-partum placenta as described above or from placental cells that have been cultured after isolating from the placenta. Cells may be isolated according to cell characteristics by, for example, flow cytometry, as described above. In an embodiment of the present invention, placental stem cells are isolated by isolating placental cells having at least one of the following characteristics:

a. positive for cell markers CD9, CD13, CD29, CD44, CD90/Thy-1, CD105/SH-2/endoglin, CD166, SH-3, SH-4, vimentin, HLA-ABC, SSEA-4, TRA-1-60, and TRA-1-81;

b. negative for cell markers CD14, CD34, CD45, AC or CD133/2, cytokeratin 7, von Willebrand factor, HLA-DR, HLA G, glycophorin A, placental alkaline phosphatase, and β-human chorionic gonadotropin; or c. positive for cell markers CD9, CD13, CD29, CD44, CD90/Thy-1, CD105/SH-2/endoglin, CD166, SH-3, SH-4, vimentin, HLA-ABC, SSEA-4, TRA-1-60, and TRA-1-81, and negative for cell markers CD14, CD34, CD45, AC or CD133/2, cytokeratin 7, von Willebrand factor, HLA-DR, HLA G, glycophorin A, placental alkaline phosphatase, and β-human chorionic gonadotropin.

The present invention also provides a method for obtaining a placental stem cell. The method comprises obtaining a post-partum placenta, preparing a single-cell suspension of placental cells, culturing the placental cells, and obtaining a placental stem cell. Post-partum placenta may be obtained, for example, with informed consent from a caesarian procedure or normal birth. The placenta may be mechanically cut into smaller pieces of tissue, for example, with scissors. A single-cell suspension may be prepared by enzymatically digesting the placenta with, for example, trypsin, chymotrypsin, lysozyme, amylase, or protease K. The placental cells thus obtained may be cultured in culture medium comprising standard medium, such as DMEM (Gibco) and 10% fetal bovine serum (selected lots, Hyclone), and may be supplemented with glucose and/or antibiotics, as appropriate. Placental stem cells may be obtained by continued culture of the placental cells in the culture medium.

The presence of placental stem cells in culture may be detected by their ability to differentiate into different cell types. For example, the cultured cells may be tested for their ability to undergo adipogenic, osteogenic, and/or neurogenic differentiation. As used herein, "differentiation" refers to the appearance of or change in one or more properties that is characteristic of a particular cell type. Such a property may include, but is not limited to, the expression of a cell marker characteristic of a particular cell type. Other properties may include the appearance of or change in cell morphology or expression of a protein characteristic of a particular cell type. Thus, for example, adipogenic differentiation refers to the appearance of one or more adipocyte-like property. Similarly, osteogenic and neurogenic differentiation refer to the appearance of one or more osteoblast and neural cell-like property. Adipocytes are connective tissue cells responsible for the synthesis and storage of fat, while osteoblasts are the primary cells responsible for bone formation and are thought to originate from osteoprogenitor cells within skeletal tissues. As used herein, "neural cells" refer to neurons or glial cells. Glial cells are further subdivided into astrocytes and oligodendrocytes. Placental stem cells may be induced to differentiate with an effective amount of a differentiation agent. An "effective amount" refers to the amount of a differentiation agent that induces differentiation of a cell. A "differentiation agent" may be any chemical, cytokine, protein, peptide, or any other substance that is capable of inducing differentiation of a cell.

Adipogenic differentiation may be induced in vitro by culturing the cells in 20% rabbit serum, a known inducer of adipogenesis in marrow stromal osteoprogenitor cells (Diascro et al., J. Bone Miner. Res. 13:96-106, 1988). Adipogenic differentiation may be detected by testing for the presence of adipogenic transcription factors PPARγ2 (peroxisome proliferator activated receptor gamma) and/or CEBPα (CCAAT/enhancer binding protein alpha), by methods such as immunohistochemistry and reverse-transcriptase polymerase chain reaction. Alternatively, adipogenic differentiation may be detected by lipid accumulation as demonstrated by Oil Red O staining after culture in an adipocyte-inducing medium (Conget and Minguell, J. Cellular Physiology 181:67-73, 1999). Other methods of inducing and detecting adipogenic differentiation may be used (see, e.g., Pittenger et al., Science 284:143-147, 1999; Tchoukalova et al., Obesity Research 8:664-672, 2000).

Osteogenic differentiation may be induced by culturing the cells in medium containing, for example, an effective amount of methylisobutylxanthine, dexamethasone, and insulin (Student et al., J. Biol. Chem. 255:4745-4750, 1980). Osteogenic differentiation may be detected by testing for the presence of osteogenic markers, which include, but are not limited to, osteopontin (OP), osteocalcin (OC), osteonectin (ON), and bone sialoprotein. Osteogenesis may also be detected by using von Kossa stain (Jaiswal et al., J Cell Biochem. 64:295-312, 1997) and/or alizarin red stain (Wan et al., Chin. J. Traumatol. 5:374-379, 2002), which detect the presence of calcium deposit activity.

The placental stem cells of the invention may also be induced to undergo differentiation into neural-like cells. The placental stem cells of the invention may be cultured in medium containing, for example, an effective amount of basic fibroblastic growth factor (b-FGF)/epidermal growth factor (EGF) (Maric et al., J. Neuroscience 23:240-251, 2003), retinoic acid (RA) (see, e.g., Durston et al., Nature 340:140-144, 1989; Hunter et al., Proc. Natl. Acad. Sci. USA 88:3666-3670, 1991), β-mercaptoethanol/dimethylsulfoxide/butylated hydroxyanisole (βME/DMSO/BHA) (Woodbury et al., J. Neurosci. Res. 61:364-370, 2000), or 1-methyl-3-isobutylxanthine (IBMX) (Deng et al., Biochem. Biophys. Res. Commun., 282:148-152, 2001) to induce neurogenic differentiation. The placental stem cells of the invention may also be induced to undergo neurogenic differentiation by co-culturing the cells with brain cells. Differentiation into neuron-like cells may be detected by testing for the presence of neuron markers, which include, but are not limited to, neuron-specific enolase (NSE), neuronal nuclei (NeuN), and microtubule-associated protein 2 (MAP2) (Jang et al., J. Neurosci. Res. 75:573-584, 2004; Rubio et al., Mol. Cell Neurosci. 16:1-13, 2000). Differentiation into astrocyte-like cells may be detected by testing for the presence of astrocyte markers, which include, but are not limited to, glial fibrillary acidic protein (GFAP) (Raff et al, J. Neurosci. 3:1289-1300, 1983). Differentiation into oligodendrocyte-like cells may be detected by testing for the presence of oligodendrocyte markers, which include, but are not limited to, the NG2 marker (Baumann et al., Physiol. Rev. 81:871-927,2001).

Of course, the placental stem cells of the present invention may be induced into other cell types by methods known in the art.

The present invention also provides a method for culturing a placental stem cell comprising obtaining a post-partum placenta, preparing a single-cell suspension of placental cells, culturing the placental cells, obtaining a placental stem cell, and culturing the placental stem cell. The placental stem cell may be cultured in the same culture medium as that used to culture the single-cell suspension of placental cells.

The present invention further provides a composition comprising a placental stem cell and/or a differentiated placental stem cell of the invention. The present invention also provides a pharmaceutical composition comprising a placental stem cell and/or a differentiated placental stem cell of the invention. The placental stem cell and/or a differentiated placental stem cell of the invention or formulations thereof may be administered by any conventional method including parenteral (e.g. subcutaneous or intramuscular) injection or intravenous infusion. The treatment may consist of a single dose or a plurality of doses over a period of time. The pharmaceutical composition may comprise one or more acceptable carriers. The carrier(s) must be "acceptable" in the sense of being compatible with the placental stem cell and not deleterious to the recipients thereof. Typically, the carriers may be water or saline which will be sterile and pyrogen free.

The placental stem cells and/or differentiated placental stem cells of the invention may also be cryopreserved. The cells may be cryopreserved in a solution comprising, for example, dimethyl sulfoxide at a final concentration not exceeding 10%. The cells may also be cryopreserved in a solution comprising dimethyl sulfoxide and/or dextran. Other methods of cryopreserving cells are known in the art.

The present invention provides a method of treating a patient, which comprises administering to the patient a therapeutically effective amount of the placental stem cell of the invention. "Therapeutically effective amount" as used herein, refers to that amount of placental stem cell that is sufficient to reduce the symptoms of the disorder, or an amount that is sufficient to maintain or increase in the patient the number of cells derived from the placental stem cell.

A patient is hereby defined as any person or non-human animal in need of treatment with a placental stem cell, or to any subject for whom treatment may be beneficial, including humans and non-human animals. Such non-human animals to be treated include all domesticated and feral mammals. In an embodiment of the present invention, the placental stem cell to be administered is obtained from the same species as the species receiving treatment. Examples of mammalian species include rodents, human, non-human primates, equines, canines, felines, bovines, porcines, ovines, lagomorphs, and the like.

The placental stem cells of the invention may be used in the treatment of any kind of injury due to trauma where tissues need to be replaced or regenerated. Examples of such trauma-related conditions include central nervous system (CNS) injuries, including injuries to the brain, spinal cord, or tissue surrounding the CNS injuries to the peripheral nervous system (PNS), or injuries to any other part of the body. Such trauma may be caused by accident, or may be a normal or abnormal outcome of a medical procedure such as surgery or angioplasty. The trauma may be related to a rupture or occlusion of a blood vessel, for example, in stroke or phlebitis. In specific embodiments, the cells may be used in autologous or heterologous tissue replacement or regeneration therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues. Injuries may be due to specific conditions and disorders including, but not limited to, myocardial infarction, seizure disorder, multiple sclerosis, stroke, hypotension, cardiac arrest, ischemia, inflammation, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis (ALS), ischemic renal disease, brain or spinal cord trauma, heart-lung bypass, glaucoma, retinal ischemia, retinal trauma, inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinuria, mucoplysaccharidenosis, chronic granulomatous disease and tyrosinemia, Tay-Sachs disease, cancer, tumors or other pathological or neoplastic conditions.

The placental stem cell used in the treatment may also contain a nucleic acid vector or biological vector in an amount sufficient to direct the expression of a desired gene(s) in a patient. The construction and expression of conventional recombinant nucleic acid vectors is well known in the art and includes those techniques contained in Sambrook et al., *Molecular Cloning: A Laboratory Manual*, Vols 1-3 (2d ed. 1989), Cold Spring Harbor Laboratory Press. Such nucleic acid vectors may be contained in a biological vector such as viruses and bacteria, preferably in a non-pathogenic or attenuated microorganism, including attenuated viruses, bacteria, parasites, and virus-like particles.

The nucleic acid vector or biological vector may be introduced into the cells by an ex vivo gene therapy protocol, which comprises excising cells or tissues from a patient, introducing the nucleic acid vector or biological vector into the excised cells or tissues, and reimplanting the cells or tissues into the patient (see, for example, Knoell et al., Am. J. Health Syst. Pharm. 55:899-904, 1998; Raymon et al., Exp. Neurol. 144:82-91, 1997; Culver et al., Hum. Gene Ther. 1:399-410, 1990; Kasid et al., Proc. Natl. Acad. Sci. U.S.A. 87:473-477, 1990). The nucleic acid vector or biological vector may be introduced into excised cells or tissues by, for example, calcium phosphate-mediated transfection (Wigler et al., Cell 14:725, 1978; Corsaro and Pearson, Somatic Cell Genetics 7:603, 1981; Graham and Van der Eb, Virology 52:456, 1973). Other techniques for introducing nucleic acid vectors into host cells, such as electroporation (Neumann et al., EMBO J. 1:841-845, 1982), may also be used.

The cells of the invention may also be co-administered with other agents, such as other cell types, growth factors, and antibiotics. Other agents may be determined by those of ordinary skill in the art.

Similarly, differentiated placental stem cells of the invention may be used to treat a patient, which comprises administering to the patient a therapeutically effective amount of the differentiated cells of the invention. The differentiated cells of the invention may contain a nucleic acid vector or biological vector and may also be co-administered with other agents, as discussed above. The differentiated cells of the invention may be used in the treatment of tissues that need to be replaced or regenerated. For example, the placental stem cells of the invention exhibiting neurogenic differentiation may be used to treat a neurodegenerative disease, such as Parkinson's disease, Alzheimer's disease, Pick's disease, Huntington's disease, and amyotrophic lateral sclerosis. The differentiated cells may also be used to treat a brain or spinal cord injury. In another embodiment, placental stem cells exhibiting adipogenic differentiation may be used to treat, for example, diabetes mellitus. In yet another embodiment, placental stem cells exhibiting chondrogenic differentiation may be used to treat degenerative joint diseases such as osteoarthritis and rheumatoid arthritis and other types of cartilage defects, such as those due to traumatic fractures. Inherited/genetic joint diseases including inherited forms of osteonecrosis of the femoral head may also be treated. In a further embodiment, placental stem cells exhibiting osteogenic differentiation may be used to treat bone defects such as those due to traumatic fractures, age-related diseases such as osteoporosis, and inherited/genetic diseases such as osteopetrosis.

Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary depending upon the desired properties sought to be obtained by the present invention. At the very least, and not as an attempt to limit the application of the doctrine of equivalents to the scope of the claims, each numerical parameter should be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements.

It must be noted that as used herein and in the appended claims, the singular forms "a", "and", and "the" include plural referents unless the context clearly dictates otherwise.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes.

All publications mentioned in this application are incorporated by reference to disclose and describe the methods and/or materials in connection with which the publications are cited. Additionally, the publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Methods, techniques, and/or protocols (collectively "methods") that can be used in the practice of the invention are not limited to the particular examples of these procedures cited throughout the specification but embrace any procedure known in the art for the same purpose. Furthermore, although some methods may be described in a particular context in the specification, their use in the instant invention is not limited to that context.

The present invention is illustrated by the following Examples, which are not intended to be limiting in any way.

EXAMPLE 1

Isolation and Culture of Placental Stem Cell

Term (38-40 wk gestation) placentas from healthy donor mothers were obtained by caesarian section or natural birth with informed consent, which permitted the use of the placenta for research purposes according to the procedures approved by the institutional review board. The placentas were carefully dissected and washed several times in phosphate-buffered saline (PBS). The harvested pieces of tissue were further cut into smaller pieces with scissors and enzymatically digested with 0.25% trypsin-EDTA (Gibco) for 10 minutes at 37° C. The cells were pelleted by centrifugation, washed once with PBS, and suspended in DMEM (Gibco) medium supplemented with 10% FBS (Hyclone), 100 U/ml penicillin (Gibco), and 100 g/ml streptomycin (Gibco). Cell cultures were maintained at 37° C. and 5% $CO_2$ and in a water-saturated atmosphere. Medium was replaced twice every week. When the plates became more than 80% confluent, the cells were recovered with 0.25% trypsin-EDTA and replated at a ratio of 1:2 to 1:3. Cells were grown for at least 9 days and analyzed.

EXAMPLE 2

Adipocytic and Osteogenic Differentiation of Placental Stem Cells

Cells obtained according to Example 1 were cultured either in an adipogenic medium (0.5 mM isobutyl-methylxanthine, 1 μM dexamethasone, 10 μM insulin, and 60 μM indomethacin) (Dennis et al., J. Bone and Mineral Research 14:700-709, 1999) or osteogenic medium (0.1μM dexamethasone, 10 mM β-glycerol phosphate and 50 μm ascorbate) (Jaiswal et al., J Cell Biochem. 64:295-312, 1997). The presence of adipocytes was assessed by the cellular accumulation of neutral lipid vacuoles that stained with Oil Red stain (Conget and Minguell, J. Cellular Physiology 181:67-73, 1999). Osteoblastic differentiation was evaluated by calcium accumulation with von Kossa stain (Jaiswal et al., J Cell Biochem. 64:295-312, 1997) or alizarin red stain (Wan et al., Chin. J. Traumatol. 5:374-379, 2002).

Figure 1B:
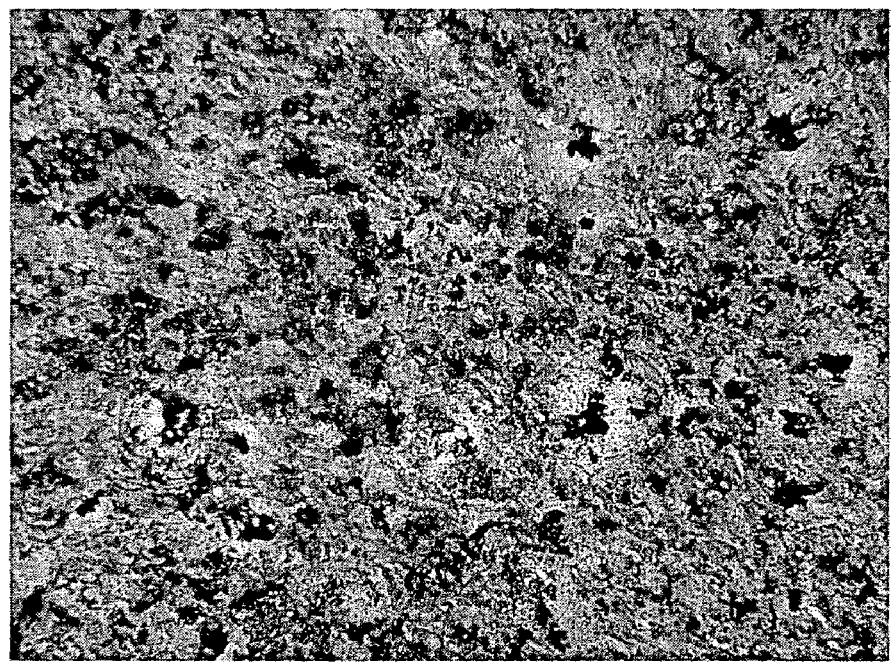
Figure 2A:
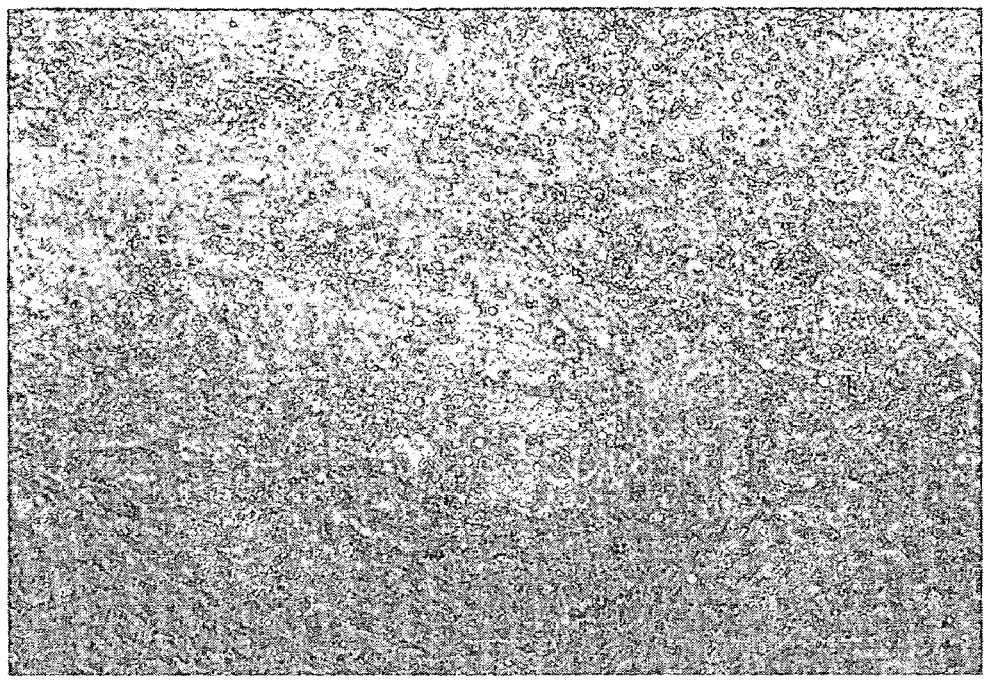
FIG. 2A shows unstained placental stem cells and FIG. 2B shows the cells stained with Oil Red to detect adipocytes (dark areas).
Figure 2B:
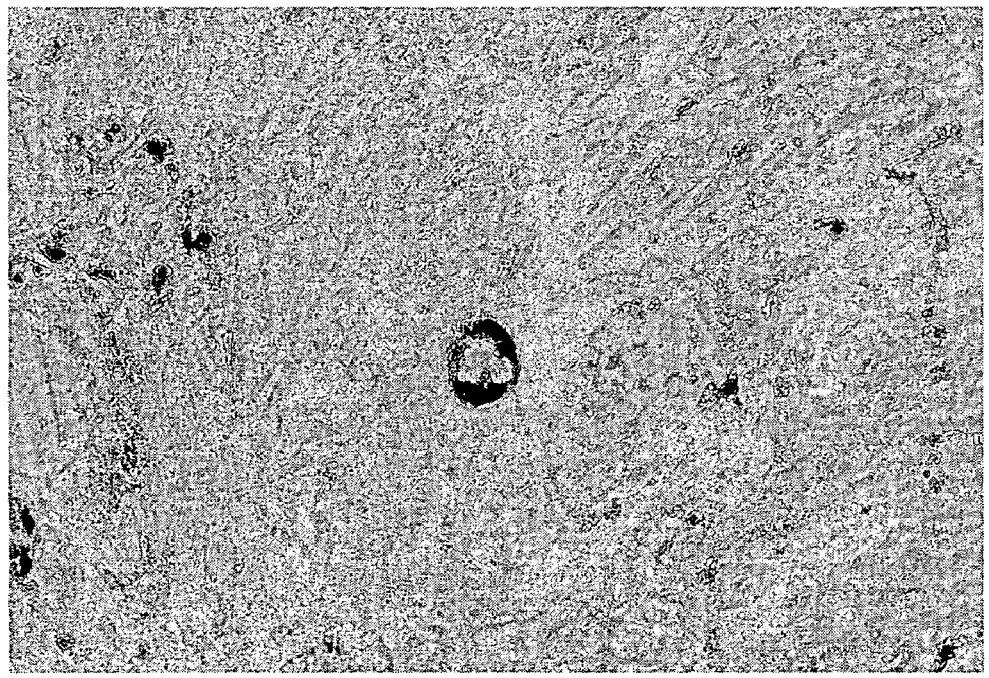
Figure 2C:
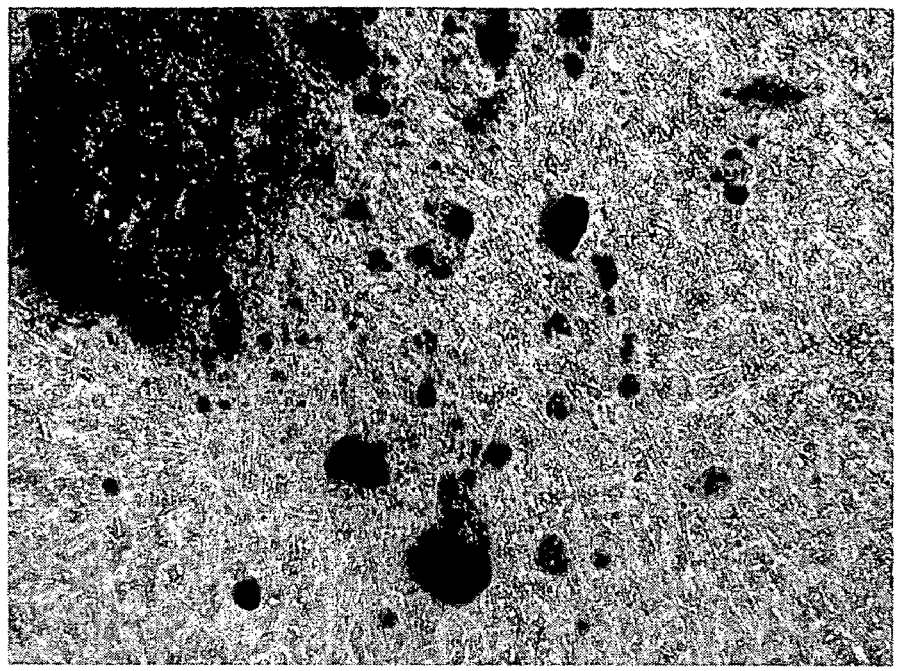
FIG. 2C shows the cells stained with alizarin red stain and FIG. 2D shows the cells stained with von Kossa stain, both of which detected osteoblasts (in red and brown, respectively, both shown as darker shaded areas) in the cultured placental stem cells.
Figure 2D:
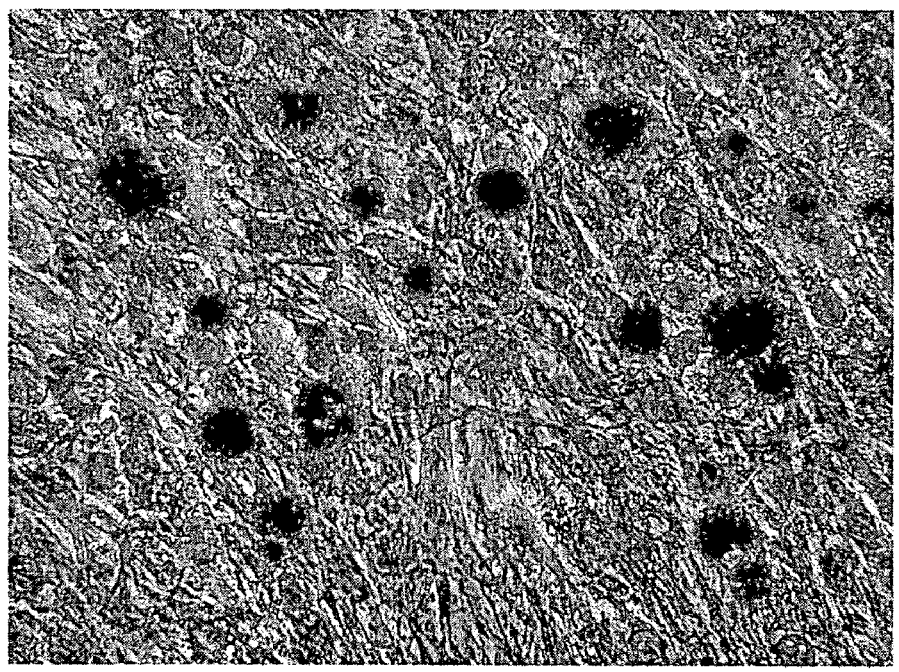

FIG. 1 shows the positive control bone marrow mesenchymal stem cells stained with Oil Red stain to detect adipocytic differentiation (FIG. 1A), and von Kossa stain to detect osteogenic differentiation (FIG. 1B). FIG. 2 demonstrates the differentiation potential of the placental stem cells of the invention. FIG. 2A shows the unstained placental stem cells after adipocytic differentiation, and FIG. 2B shows the placental stem cells after adipocytic differentiation stained with Oil Red to detect intracellular lipid accumulations. FIG. 2B shows that the placental stem cells obtained according to the method of the invention are able to differentiate into adipocytes. The placental stem cells of the invention are also able to differentiate into osteoblasts, as indicated by FIGS. 2C and 2D. Both alizarin red staining (FIG. 2C) and von Kossa staining (FIG. 2D) resulted in the staining of osteoblasts from the cultured placental stem cells. Thus, the placental stem cells are able to undergo differentiation into multiple cell types.

EXAMPLE 3

Chondrogenic Differentiation of Placental Stem Cells

A chondroblast is a cell that secretes cartilage matrix and becomes a chondrocyte when it is surrounded by matrix. Placental stem cells obtained according to Example 1 above were induced to undergo chondrogenic differentiation using the micromass culture technique of Barry et al., Experimental Cell Research 269:189-200, 2001 and Zuk et al., Tissue Engineering 7:211-28, 2001. Briefly, approximately 200,000 cells were placed in a 15 ml conical polypropylene tube for 3 to 6 hours in medium containing 10 ng/ml transforming growth factor (TGF)-β1 or TGF-β3 (both from R&D systems), 0.1 mM ascorbic acid-2-phosphate (Sigma), 1×107 M dexamethasone (Sigma), and 1% insulin-transferrin-sodium selenite media supplement (Sigma). The cells were transferred to 24-well plates and further cultured for two to three weeks. The cells were then stained with Alcian Blue (pH1) (Sigma) for proteoglycans, which are found in cartilage and other connective tissues. Additionally, Type II collagen was detected in the cultured cells by immunocytochemistry using anti-human collagen type II antibodies (Santa Cruz Biotechnology, Inc.) at a 1:100 dilution after overnight incubation at 4° C. Subsequent secondary antibody staining was performed using biotinylated anti-goat IgG secondary antibodies (1:500 dilution, ABC kit, Vector Labs) for 45 minutes at room temperature. Visualization was performed using a Leica DM IRB inverted microscope (Leica, Germany).

Figure 3A:
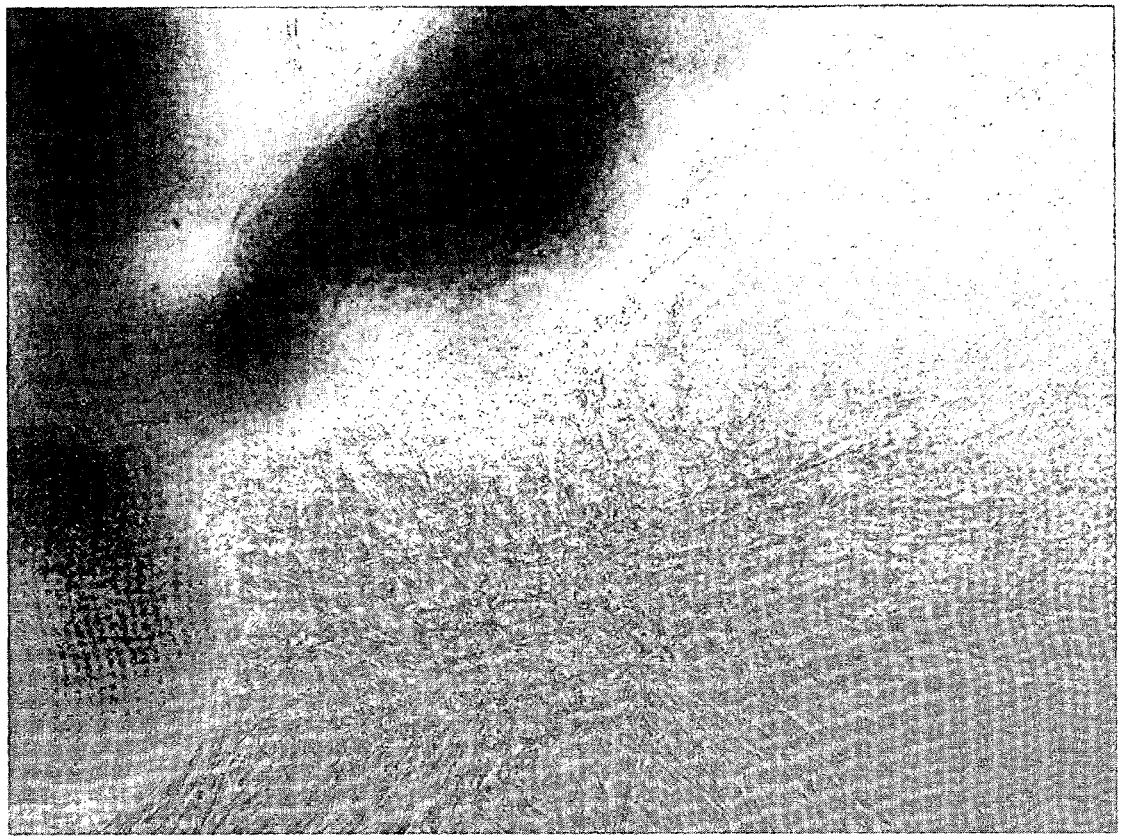
FIG. 3A shows a placental stem cell-derived cell that stained blue with Alcian Blue dye (darker areas within the cell), indicating that the cell produced proteoglycans.
Figure 3B:
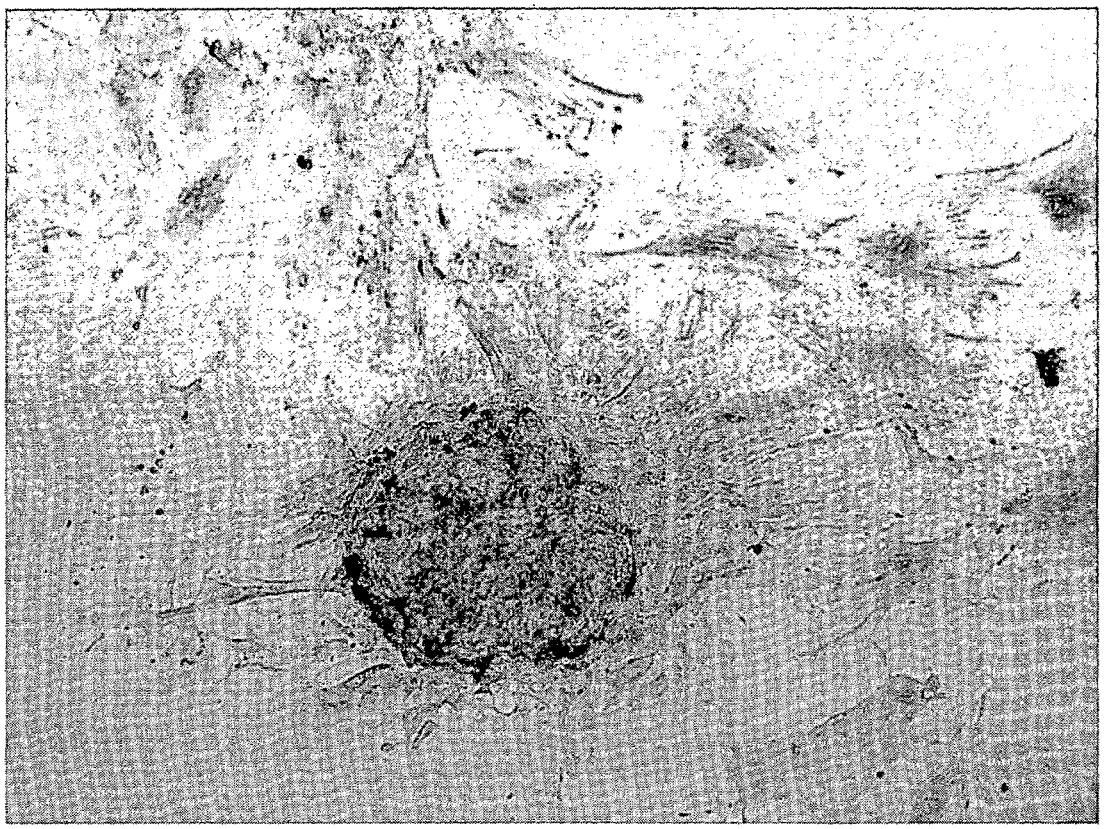
FIG. 3B shows a placental stem cell-derived cell that reacted with anti-Type II collagen antibody (darker areas).

FIGS. 3A and 3B confirm that the placental stem cells of the invention have chondrogenic potential. Specifically, FIG. 3A shows a placental stem cell-derived cell that stained blue with Alcian Blue dye, indicating that the cell produced proteoglycans. FIG. 3B also shows a placental stem cell-derived cell that reacted with anti-Type II collagen antibody, indicating that the cell produced Type II collagen, which is a molecule found mostly in cartilage and which is essential for the normal development of bones and other connective tissues.

EXAMPLE 4

Phenotypic Characterization of Placental Stem Cells

The placental stem cells obtained in Example 1 were analyzed for cell markers by flow cytometry and/or immunochemical staining.

Table 1 shows a comparison of the cell markers tested on bone marrow (BM) according to Pittenger et al. (Science 284:143-147, 1999) and Reyes et al., (Blood 98:2615-1625, 2001), umbilical cord blood (UCB) according to Erices et al., (Br. J. Haematol. 109:235-242, 2000), and placental stem cells obtained in Example 1 (MPSC).

TABLE 1

| Cell Markers | Pittenger et al (Bone marrow) | Reyes et al (Bone marrow) | Erices et al (UCB) | MPSC |
|---|---|---|---|---|
| CD9 | (+) | | | (+) |
| CD13 | | (+) | (+) | (+) |
| CD14 | (−) | | (−) | (−) |
| CD29 | (+) | | (+) | (+) |
| CD34 | (−) | (−) | (−) | (−) |
| CD44 | (+) | (+) | | (+) |
| CD45 | (−) | (−) | (−) | (−) |
| CD90/Thy-1 | (+) | | (+) | (+) |
| CD105/SH2/endoglin | (+) | | | (+) |
| CD117/c-kit | | (−) | | (−) |
| AC or CD133/2 | | | | (−) |
| CD166 | (+) | | | (+) |
| SH3 | (+) | | (+) | (+) |
| SH4 | (+) | | (+) | (+) |
| Vimentin | | | | (+) |
| Cytokeratin 7 | | | | (−) |
| von Willebrand factor | (−) | | (−) | (−) |
| HLA-ABC | (+) | (−) | | (+) |
| HLA-DR | (−) | (−) | | (−) |
| HLA-G | | | | (−) |
| Glycophorin A | | (−) | | (−) |
| SSEA-4 | | | | (+) |
| TRA-1-60 | | | | (+) |
| TRA-1-81 | | | | (+) |
| β-human chorionic gonadotropin | | | | (+) |
| Placental alkaline phosphatase | | | | (−) |

EXAMPLE 5

Further Characterization of Placental Stem Cells

The placental stem cells obtained according to Example 1 were again analyzed by flow cytometry, immunochemistry and immunofluorescence, and/or reverse transcriptase polymerase chain reaction (RT-PCR).

Flow cytometry. Flow cytometry was performed with the FACSCalibur (BD Biosciences, San Jose, Calif., USA). Placental stem cells after the fifth passage were trypsinized and labeled with fluoroscein isothiocyanate (FITC)-conjugated anti-CD14 or anti-CD90; phycoerythrin (PE)-conjugated anti-CD45; or unconjugated anti-CD34 (BD Biosciences), anti-STRO-1 (Hybridoma bank, U. of Iowa, Iowa, USA), or anti-CD105/SH2 (Hybridoma bank). FITC conjugated rat anti-mouse IgG Ab (BD Biosciences) was used as the secondary antibody when appropriate.

Figure 4:
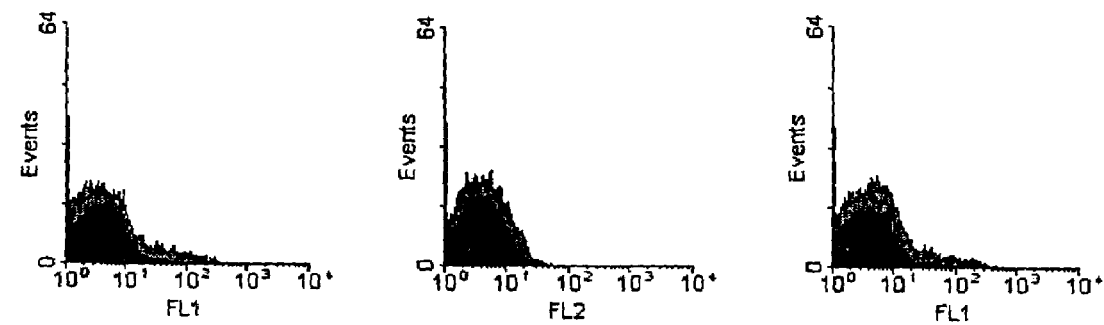
FIG. 4 FIG. 4 shows histograms of CD14, CD45, CD34, CD90, CD105, and STRO-1 expression on undifferentiated placental stem cells.
Figure 4:
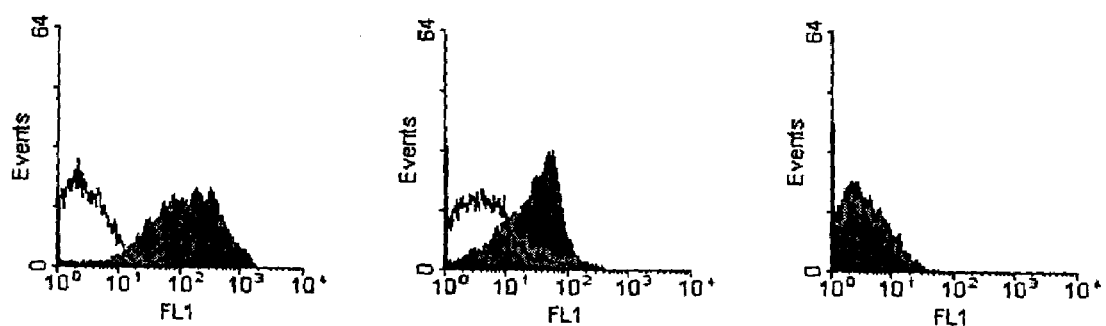

FACS analysis (FIG. 4) confirmed that undifferentiated placental stem cells were negative for CD14, CD45, and CD34—all hematopoietic markers. The placental stem cells were also negative for STRO-1, a bone marrow stromal precursor cell marker. Thus, the placental stem cells are unlikely to be of hematopoietic origin or contaminated with umbilical cord blood cells. The placental stem cells were further confirmed as expressing CD90, a surface marker that is also observed on bone marrow mesenchymal stem cells (MSCs), and for CD105. The morphology of the placental stem cells were similar to MSCs, appearing spindle-shaped, with fibroblast-like colonies adhering to plastic surfaces.

Immunocytochemistry and immunofluorescence and RT-PCR. Cultured cells were fixed with 4% paraformaldehyde for 5 minutes at room temperature and permeabilized with 0.1% Triton-X 100 for 20 minutes. Slides were then incubated sequentially with primary antibody overnight at 4° C. For immunocytochemistry, primary antibodies against NSE (Sigma) (1:25) was applied, followed by biotinylated anti-rabbit antibody and an avidin-biotin conjugate of hourseradish peroxidase (Vector Laboratories, Burlingame, Calif., USA). For immunofluorescence staining, primary antibodies against NeuN (Chemicon International Inc., Temecula, Calif., USA) (1:100), Nestin (BD Biosciences) (1:100), GFAP (glial fibrillary acidic protein, Chemicon International Inc.) (1:100), MAP2 (microtubule-associated protein 2, Chemicon International Inc.) (1:200), and NG2 (Chemicon International Inc.) (1:50) were used. Cy3 or fluorescein-labeled secondary antibodies were then applied for 1 hour at 37° C., and stained with 4', 6-diamino-2-phenylindole (DAPI) (KPL Inc. Gaithersburg, Mass., USA) to identify cell nuclei. Cells were visualized by confocal fluorescence microscopy (Zeiss, LSM 510).

For RT-PCR, total RNA was isolated from cultured cells using Purescript (Gentra System, Minneapolis, Minn., USA), and 2 μg of total RNA was used for reverse transcription using Superscript II (Invitrogen, Carlsbad, Calif., USA). The cDNA was synthesized using Taq Platinum (Invitrogen) and 0.025 μg/μl oligo(dT). An equal volume of each sample was used to amplify human genes with 1 μM of each of the following primers: for the human nestin gene 5'-CCC TGA CCA CTC CAG TTT A-3' and 5'-GAG TCC TGG ATT TCCTTC-3'; for the human Oct-4 gene 5'-GTG AAG CTG GAG AAG GAG AAG CTG-3' and 5'-CAA GGG CCG CAG CTT ACA CAT G-3'; and for the neurofilament light-chain (NF-L) gene 5'-CCC GAC TCA GTT TCA CC-3' and 5'-CAG CCT TAG ACG CCT C-3'. Human glyceraldehyde-3-phosphate dehydrogenase (GAPDH) primers (Clontech, Palo Alto, Calif., USA) were used as internal controls for the PCR reactions. The cDNA from each sample was amplified for 30 cycles (1 min at 94° C., 1 min at 65° C., and 1 min at 72° C.). The PCR products were then separated by electrophoresis on 1.5% agarose gels. The sequence of each PCR product was confirmed using automatic sequencing.

Figure 5:
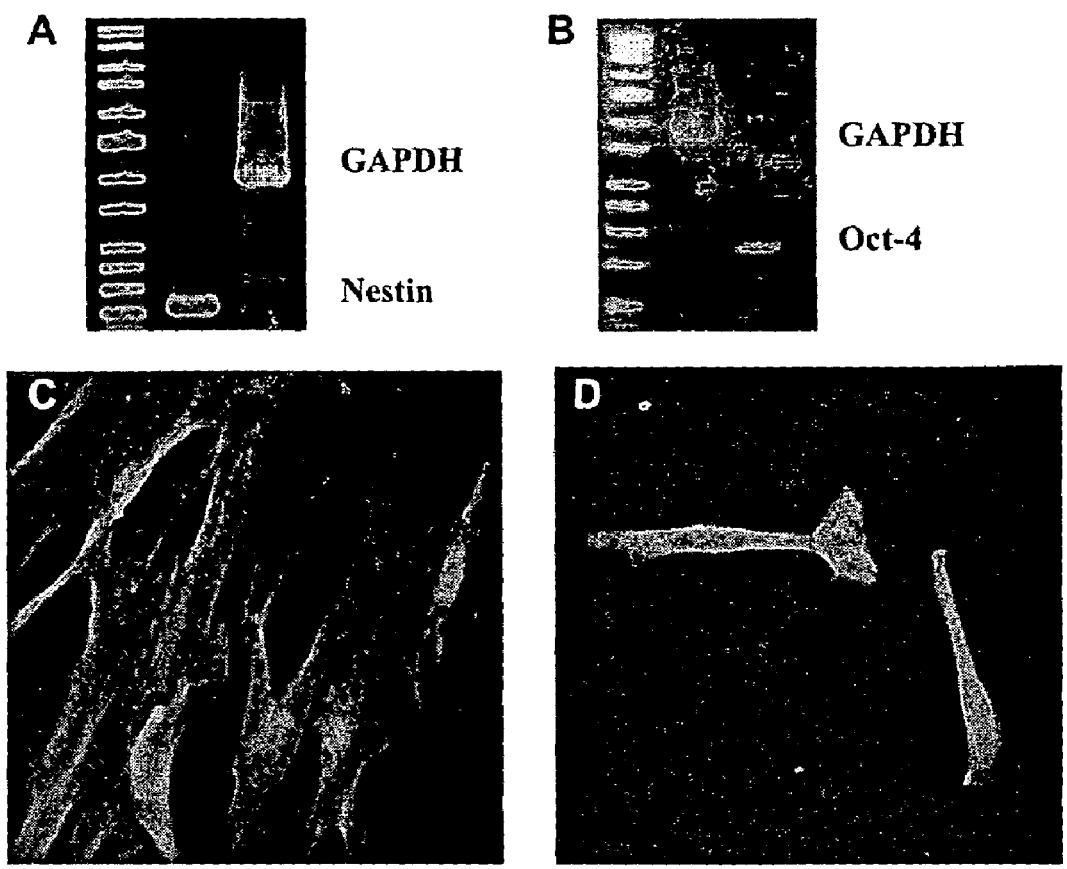
FIG. 5 FIG. 5 shows the expression of Nestin and Oct-4 in placental stem cells.
Figure 6:
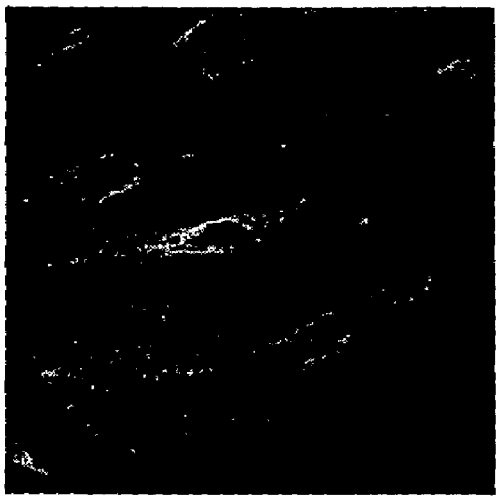
FIG. 6 FIG. 6 shows placental stem cells tested for Tuji1 ($\beta$-tubulin III), GFAP, and NeuN expression and detected by immunofluorescence using confocal microscopy. The cell nuclei were counterstained with DAPI. Photographs were taken at a magnification of 400×.
Figure 6:
Figure 6:
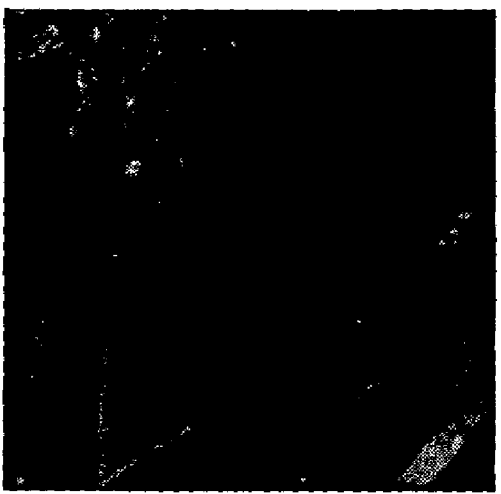

RT-PCR analysis and immunofluorescent staining of undifferentiated placental stem cells revealed that the placental stem cells were also positive for nestin (FIG. 5A, 5C), a marker for neural cells (Lendahl et al., Cell, 60:585-595, 1990), and Oct-4 (FIG. 5B, 5D), an embryonic stem cell marker (Reubinoff et al., Nature Biotech. 18:399-404, 2000). Undifferentiated placental stem cells were also weakly positive for the early neural marker Tuj1 (β-tubulin III), GFAP, and NeuN (FIG. 6).

The placental stem cells of the invention are distinct from other stem cells that have been shown to undergo neurogenic differentiation. For example, stem cells from human adipose tissue are STRO-1 positive (Zuk et al., Mol. Biol. Cell., 13: 4279-4295, 2002) whereas the placental stem cells of the invention are not. Furthermore, the placental stem cells are strongly positive in CD90, a surface marker which is absent in umbilical cord blood-derived multipotent stem cells (Goodwin et al., Biol. Blood Marrow Transplant., 7:581-588, 2001; Lee et al., Blood, 103:1669-1675, 2004). The placental stem cells are also positive for Oct-4, and several other embryonic stem cell markers, suggesting that they may represent a distinct and primitive population of multipotent stem cells.

EXAMPLE 6

Neurogenic Differentiation of Placental Stem Cells

Placental stem cells obtained according to Example 1 were plated on 35 mm culture dishes without coating, or if coated, with fibronectin, gelatin, or poly-L-Lysine (Sigma). Cells were cultured in serum-free DMEM-LG (Gibco) at various densities and exposed to either 10 ng/ml basic fibroblastic growth factor (b-FGF)/20 ng/ml epidermal growth factor (EGF) (both from R&D), retinoic acid (RA) (Sigma) at $10^{-6}$M, β-mercaptoethanol/dimethysulfoxide/butylated hydroxyanisole ($1\times10^{-5}$M βME/2% DMSO/100 µM BHA) (Sigma), or 0.5 mM 1-methyl-3-isobutylxanthine (IBMX, Sigma) for 3 to 6 days. Cells were then harvested for RT-PCR and immunocytochemical analysis as described above.

Differentiation to neural-like cells was quantified as a percentage of the total number of platelet stem cells grown under differentiation conditions. Cells were stained for NSE expression and analyzed under an invert microscope. Five non-overlapping low power images were captured from each sample. Cells exhibiting retracted cell bodies and positive NSE staining were counted as positive neural cells. Total cell count was determined by staining with 4',6-diamidino-2-phenylindole (DAPI), which stains nuclei specifically, or with anti-human nuclei antibody (1:50) (Chemicon International Inc.).

Figure 7:
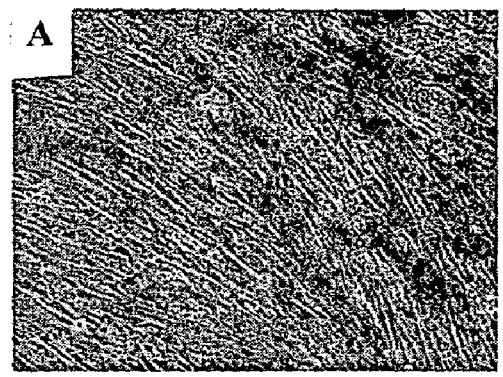
FIG. 7 FIG. 7 shows photographs of placental stem cells taken three days after being cultured in various medium.
Figure 7:
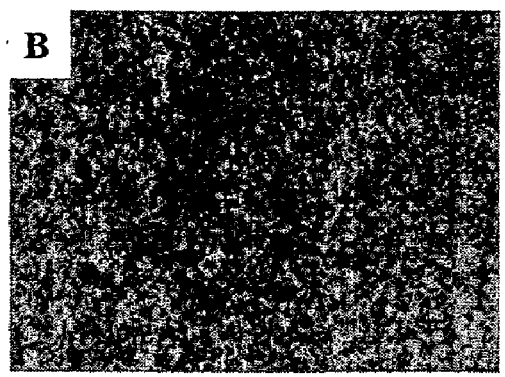
Figure 7:
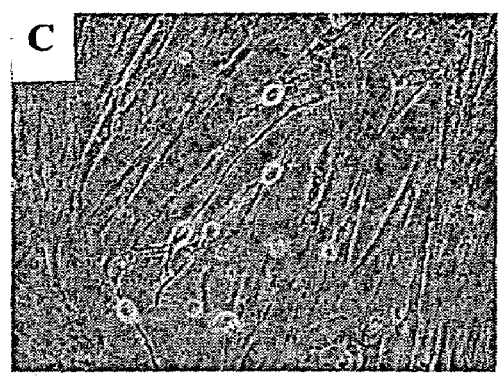
Figure 7:
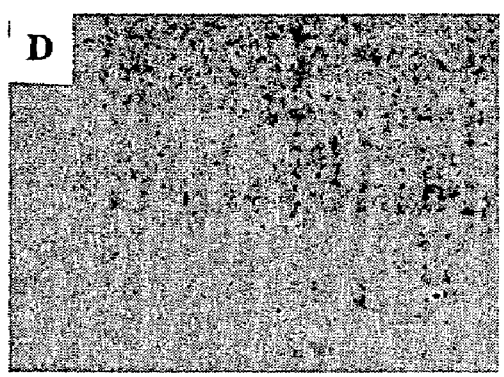
Figure 7:
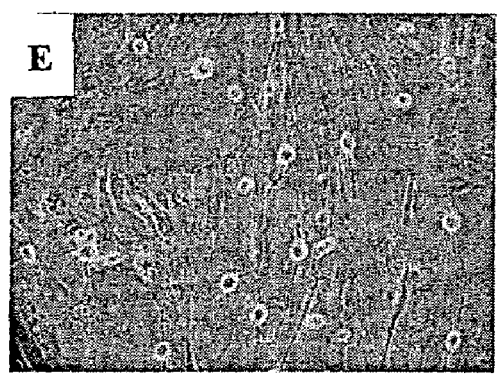
Figure 7:
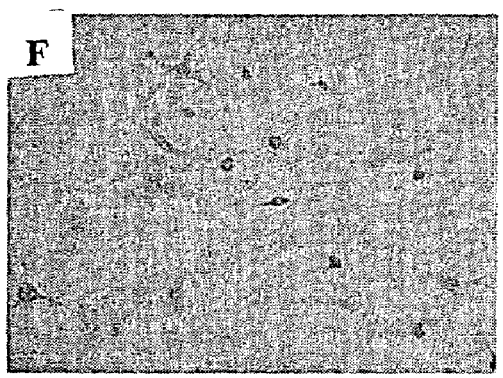

After 3 to 6 days in medium containing RA ($10^{-6}$M) or IBMX (0.5 mM), morphological changes of some of the placental stem cells were observed. Specifically, the cytoplasm of cells with retracted and extensions were observed in cells cultured in RA (FIG. 7C) and in IBMX (FIG. 7E) compared with cells cultured in expansion medium (DMEM (Gibco) supplemented with 10% FBS (Hyclone), 100 U/ml penicillin (Gibco), and 100 g/ml streptomycin (Gibco)) (FIG. 7A). In addition to morphological changes, cells cultured in RA or in IBMX also expressed higher levels of NSE, a neuronal marker, compared with control cells (FIGS. 7D, 7F and 7B, respectively). No such changes were observed on control cells and on cells cultured in b-FGF/EGF or in βME/DMSO/BHA (data not shown). After 6 days of incubation, IBMX-treated cultures showed 40%~60% differentiation into neural-like cells, whereas RA-treated cultures showed about 10% differentiation (data not shown). Moreover, IBMX-treated cells staining strongly positive for NSE showed bipolar or multipolar morphologies with long branches. Occasionally, several neural-like cells formed a net-like structure under light microscopy.

Figure 8:
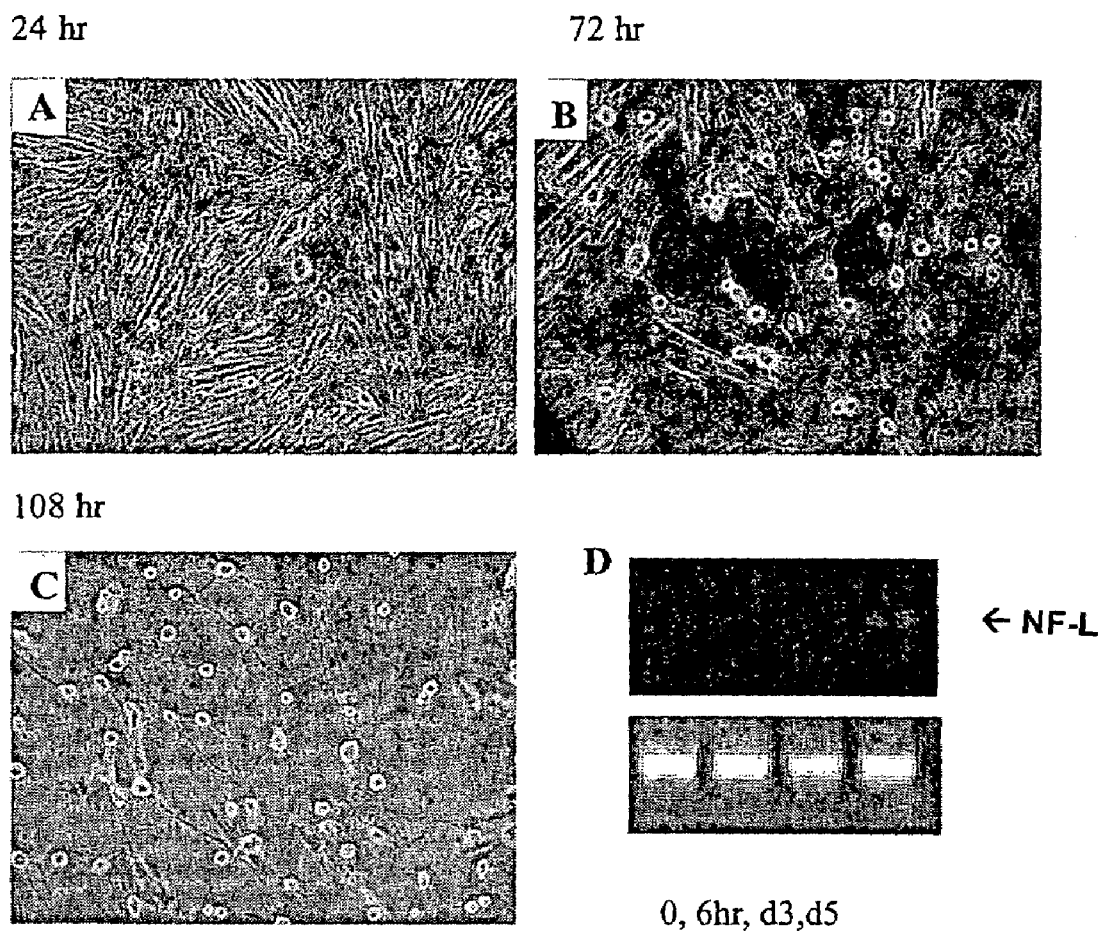
FIG. 8 FIG. 8 shows placental stem cells that had been treated with IBMX and expression of neural filament light chain (NF-L) by RT-PCR.

As early as 2 hours after incubation in IBMX treatment, morphological changes could be seen in a portion of placental stem cells (data not shown). The number of differentiated cells increased along with increasing cultivation time (FIGS. 8A-C). Based on three independent experiments, 7% of the placental stem cells had differentiated after 24 hours of treatment with IBMX and increased to more than 40% after 5 days. Furthermore, the expression of neural filament light chain (NF-L), a marker for mature neurons, was detected by RT-PCR in after five days of IBMX treatment (FIG. 8D).

Figure 9:
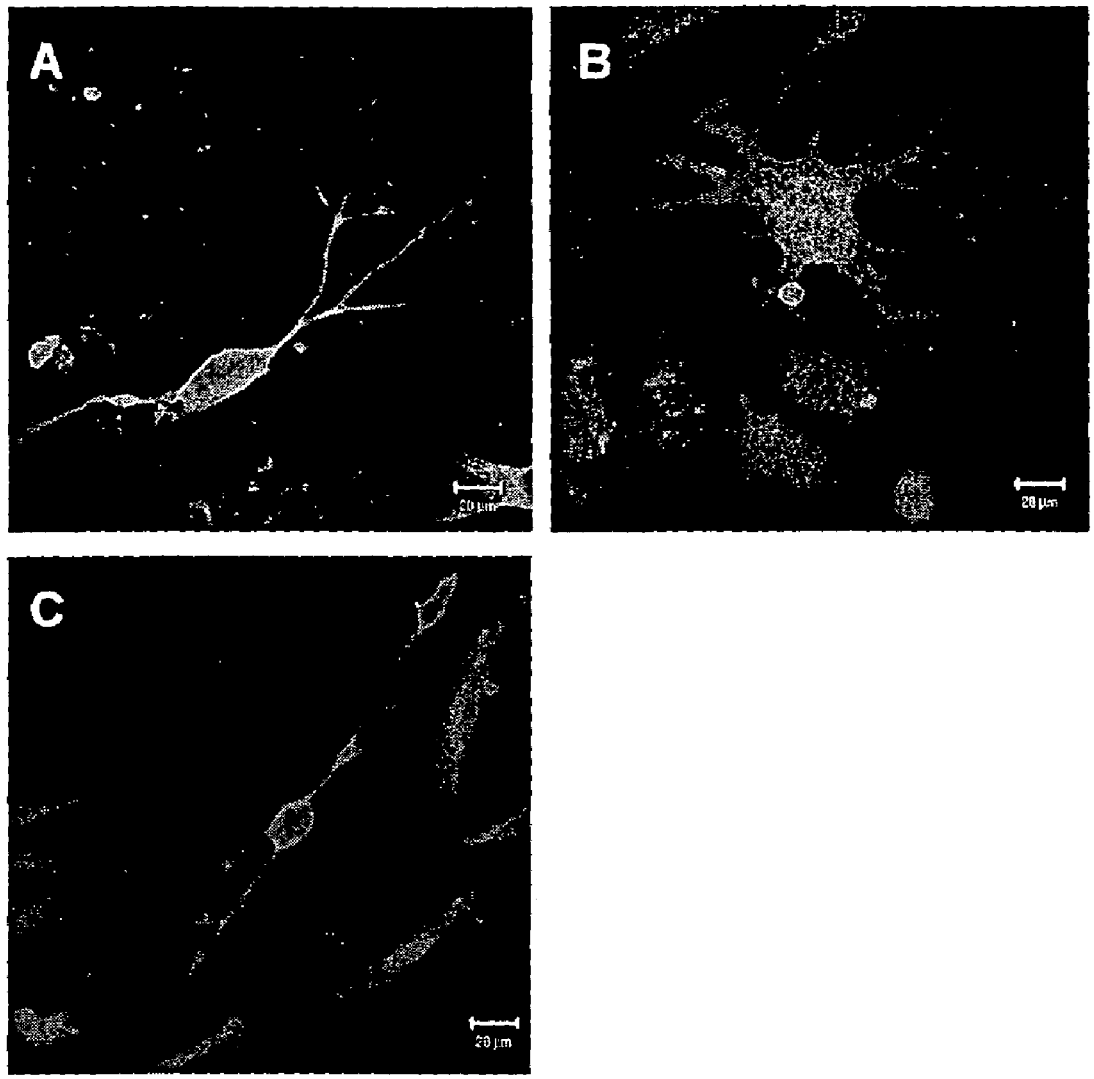
FIG. 9 FIG. 9 shows immunofluorescence of placental stem cells three days after being cultured in the presence of IBMX and tested for various markers.

Placental stem cell cultures treated with IBMX contained cells expressing the neuron marker MAP2 (FIG. 9A), the astrocyte marker GFAP (FIG. 9B), or the oligodendrocyte marker NG2 (FIG. 9C), suggesting that the placental stem cells could be differentiated into all three neural cells (neurons, astrocytes, oligodendrocytes). In addition, MAP2-positive cells displayed neuron-like morphology of condensed cell bodies with outgrowth of a few processes (FIG. 9A). Neurons, astrocytes, and oligodendrocytes comprised approximately 16%, 1%, and 17%, respectively, of the total cell count. These results are in contrast to those of Deng et al. (Biochem. Biophys. Res. Commun., 282:148-152, 2001), who reported that IBMX-treated human marrow stromal cells showed increased expression of NSE, but no expression of GFAP.

The seeding concentration of placental stem cells (up to $1\times10^3$ cells/cm$^2$) had no effect on IBMX-induced differentiation, suggesting, without being bound to theory, that neural differentiation induced by IBMX is independent of cell growth arrest. However, a dose-dependent effect of IBMX was observed (data not shown), although very high concentrations of IBMX (>0.5 mM) may cause cell death. Removal of IBMX from the culture medium caused reversion of the cells to their original phenotype (data not shown).

Placental stem cells were also induced to undergo neural differentiation by co-culturing with neonatal rat brain cultures. Rat brain primary culture for co-culture was prepared from the brain cortex of 3-day old neonatal rats (Wistar) under sterile conditions. Brain tissue was dissected and placed in DMEM (Gibco). Autoclaved slides were used to disperse cells mechanically and then trypsin-EDTA was used to dissociate the cells. After centrifugation at 1100 r.p.m. for 5 minutes, the cell pellet was resuspended in DMEM supplemented with 10% FBS, 100 U/ml penicillin, and 100 µg/ml streptomycin. These cells were maintained at 37° C. with 5% $CO_2$ for approximately 7 days.

The brain cells were then trypsinized and plated in 6-well plates at a density of $2\times10^4$ cells/cm$^2$ in DMEM-LG (Gibco). Undifferentiated placental stem cells were labeled with Cell Tracker CM-Dil (Molecular Probes, Eugene, Oreg., USA) according to the manufacturer's recommendations in order to distinguish them from the brain cells. After 24 hours, CM-Dil labeled undifferentiated PDMCs were added in wells containing the brain cells at a density of $2\times10^4$ cells/cm$^2$ in DMEM-LG (Gibco). Cells were grown in co-culture for 3 to 5 days and then immunofluorescence staining was performed to detect MAP2 and GFAP expression.

Figure 10:
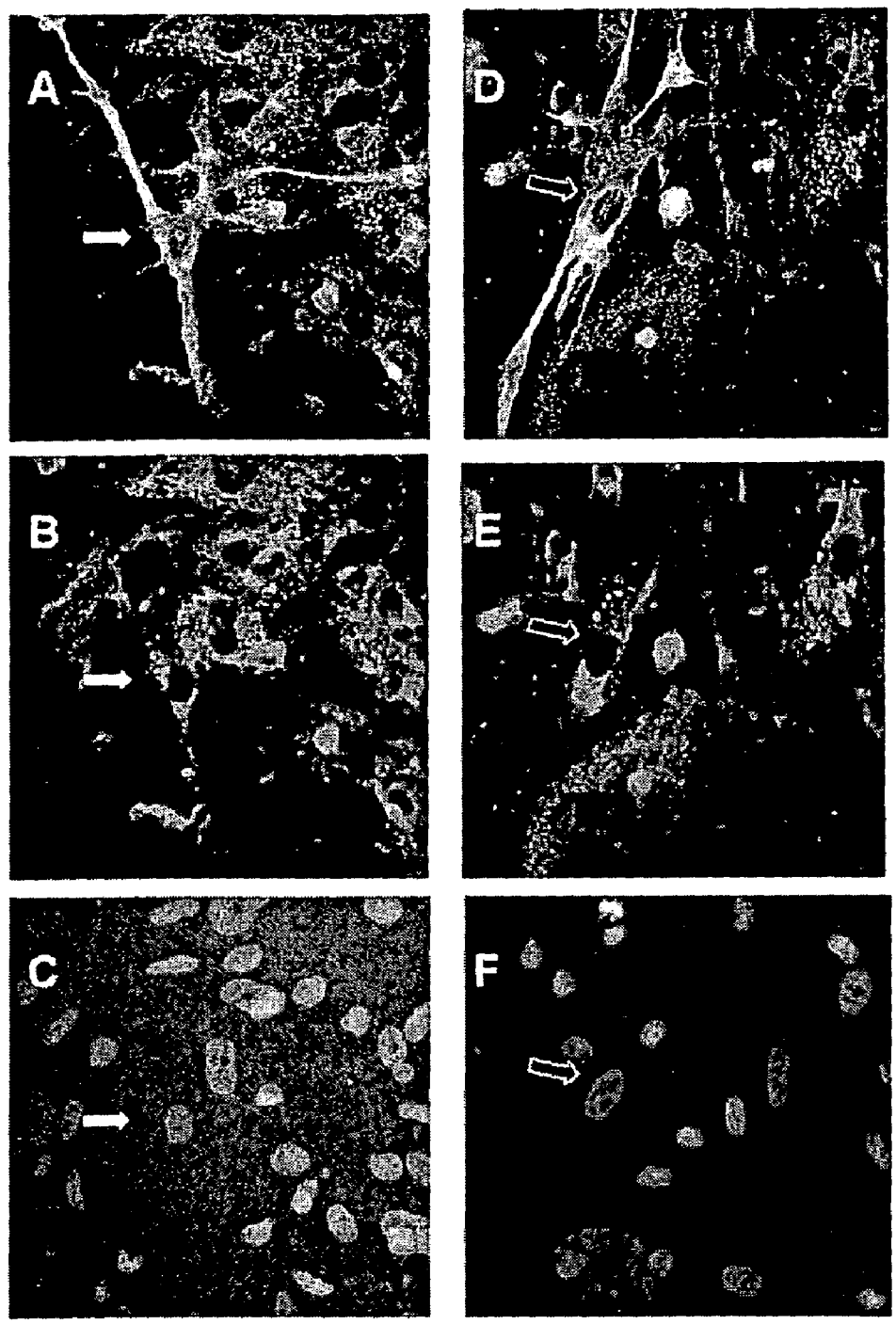
FIG. 10 FIG. 10 shows photographs of placental stem cells labeled with CM-Dil that were co-cultured with rat primary brain cells for 5 days. Photographs were taken at a magnification of 400×.

Placental stem cells co-cultured on a monolayer of neonatal rat primary brain cells could be clearly identified by their fluorescence from the Cell Tracker CM-Dil label under fluorescence microscopy (FIGS. 10B and 10E). CM-Dil labeled cells showed MAP2 expression (FIG. 10A), and as well as GFAP expression (FIG. 10D). FIGS. 10C and 10F show the nuclei of MAP2-positive and GFAP-positive CM-Dil-labeled cells stained with DAPI. The white arrow in FIG. 10C points to a placental stem cell that had differentiated into a neuron phenotype and the open arrow in FIG. 10F points to a placental stem cell that had differentiated into an astrocyte phenotype.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with the true scope and spirit of the invention being indicated by the following claims.

What is claimed is:

1. A method for neurogenic differentiation of human placental stem cells, comprising culturing the placental stem cells in a medium comprising an effective amount of 1-methyl-3-isobutylxanthine to obtain cells having at least one characteristic of a neural cell, wherein epidermal growth factor (EGF) and basic fibroblast growth factor (bFGF) are not added to the medium and wherein the cells obtained express neuron-specific enolase (NSE) and microtubule-associated protein 2 (MAP2).

2. The method of claim 1, wherein the cells obtained express the neuron-specific nuclear protein (NeuN).

3. The method of claim 1, wherein the cells obtained express the glial fibrillary acidic protein (GFAP).

4. The method of claim 1, wherein the cells obtained express the oligodendrocyte marker NG2.

5. A method of preparing a population of cells having at least one characteristic of a neural cell, comprising culturing human placental stem cells in a medium comprising an effective amount of 1-methyl-3-isobutylxanthine to obtain cells having at least one characteristic of a neural cell and isolating the population of cells, wherein epidermal growth factor (EGF) and basic fibroblast growth factor (bFGF) are not added to the medium and wherein the cells obtained express neuron-specific enolase (NSE) and microtubule-associated protein 2 (MAP2).

* * * * *